United States Patent [19]

Emami

[11] Patent Number: 6,143,768

[45] Date of Patent: Nov. 7, 2000

[54] FURAN DERIVATIVES, SYNTHESIS METHOD AND USE AS AROMA ENHANCER

[75] Inventor: Imam Emami, Paris, France

[73] Assignees: Francaise d'Aromes et Parfums; Akbar Emami, both of Chatillon, France

[21] Appl. No.: 09/367,486

[22] PCT Filed: Dec. 17, 1998

[86] PCT No.: PCT/FR98/02772

§ 371 Date: Nov. 29, 1999

§ 102(e) Date: Nov. 29, 1999

[87] PCT Pub. No.: WO99/31080

PCT Pub. Date: Jun. 24, 1999

[30] Foreign Application Priority Data

Dec. 17, 1997 [FR] France .................. 97 16026

[51] Int. Cl.[7] ............ A61K 31/445; C07D 307/66; A23L 1/226
[52] U.S. Cl. ............ 514/326; 546/214; 426/537
[58] Field of Search ............ 514/326; 546/214; 426/537

[56] References Cited

FOREIGN PATENT DOCUMENTS 0 398 417  11/1990  European Pat. Off. .
0 784 936   7/1997  European Pat. Off. .

OTHER PUBLICATIONS

Washino et al. "<Manufacture of hydroxfuranosnes fro flavoring materials" CA 111:97064, 1987.

Shigematsu, "Components of roasting flavor formed in the heating reaction between amino compounds and sugars" Nippo Sembai Kosha Chuo kenkyusho Kenkyu Hokoku, v. 118, pp. 119–182, 1976.

*Primary Examiner*—Ceila Chang
*Attorney, Agent, or Firm*—Young & Thompson

[57] ABSTRACT

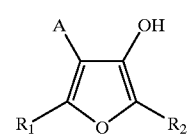

(I)

The invention concerns a compound of formula (I) in which A is a piperidin-1-yl group non-substituted or substituted by one or several groups selected among a $C_1$–$C_4$ alkyl group and a hydroxy group; $R_1$ and $R_2$, identical or different, are selected among a hydrogen atom, a $C_1$–$C_4$ alkyl group and a hydroxy group and their edible salts.

10 Claims, No Drawings

FURAN DERIVATIVES, SYNTHESIS METHOD AND USE AS AROMA ENHANCER

This application is a 371 of PCT/FR98/02772 filed Dec. 17, 1998.

The present invention relates to new furan derivatives, to processes for their synthesis and to their use as flavour enhancer.

SUMMARY

The subject of the present invention is compounds of formula I:

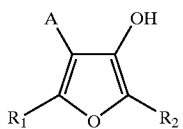

(I)

wherein A is a piperidin-1-yl group which is unsubstituted or substituted with one or more groups chosen from a $(C_1-C_4)$ alkyl group and a hydroxyl group;

$R_1$ and $R_2$, which are identical or different, are chosen from a hydrogen atom, a $(C_1-C_4)$alkyl group and a hydroxyl group, as well as their edible salts.

Preferably, the subject of the present invention is a compound of formula I in which A is an unsubstituted piperidin-1-yl group and $R_1$ and $R_2$, which are identical, represent a methyl group.

The said preferred compound is therefore 4-hydroxy-2,5-dimethyl-3-piperidylfuran

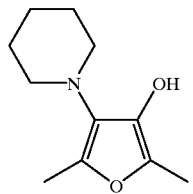

The subject of the present invention is also a process for the synthesis of the compounds of formula I as defined above, which consists in reacting a piperidine of formula AH, where A is as defined above, with a compound of formula II:

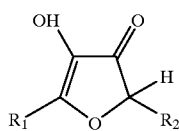

(II)

wherein $R_1$ and $R_2$, which are identical or different, are chosen from a hydrogen atom, a $(C_1-C_4)$alkyl group and a hydroxyl group, in order to obtain a compound of formula I as defined above.

DETAILED DESCRIPTION

More particularly, the 4-hydroxy-2,5-dimethyl-3-piperidylfuran may be obtained from L-rhamnose, which is reacted with piperidine, the 4-hydroxy-2,5-dimethyl-3(2H) furanone formed reacting with the piperidine.

According to a preferred embodiment of the present invention, the 4-hydroxy-2,5-dimethyl-3-piperidylfuran may be prepared according to the method comprising the steps consisting in:

bringing into contact L-rhamnose in a solution, piperidine and acetic acid in molar proportions 1.65/1/2.2;

stirring and heating the reaction mixture until the acetic acid and the solvent have evaporated off;

hydrating and then basifying the remaining reaction mixture; and extracting the 4-hydroxy-2,5-dimethyl-3-piperidylfuran by adding an organic solvent, and then washing with water, acidifying the aqueous phase and then evaporating the organic solvent.

The authors of the present invention have discovered that the compounds of formula I as defined above exhibit a flavour enhancing property.

Edible and nontoxic, the compounds of the invention are therefore useful as flavour or taste enhancers in food preparations. Among the preferred food preparations, there may be mentioned in particular preparations of the drinks, yoghurt, ice-cream and confectionery type, and the like.

The compounds of the present invention may more particularly be used in combination with at least one flavour, for example in combination with 4-hydroxy-2,5-dimethyl-3 (2H)furanone (strawberry, caramel, pineapple flavour), vanallin (vanilla flavour) or maltol (caramel flavour).

The compounds of the present invention may be used in a concentration of 5 to 50 ppm, preferably of 8 to 20 ppm in the food preparation.

When they are combined with a flavour, the compounds of the present invention may in particular be used in a proportion of about 1 to 10%, preferably of about 3 to 4% relative to the flavour.

The compounds of the present invention may be dissolved in a solvent, optionally in combination with at least one flavour.

Alcoholic solvents, such as for example ethyl alcohol, isopropyl alcohol or monopropylene glycol, are preferred solvents.

The subject of the present invention is therefore also a composition comprising a compound of formula I as defined above, in combination with at least one flavour, in a preferably alcoholic solvent. More particularly, the subject of the present invention is a composition as defined above, in which the said compound of formula I is present in a proportion of 1 to 10% relative to the said flavour.

The following examples illustrate the invention without limiting the scope thereof.

EXAMPLE 1

Synthesis of 4-Hydroxy-2,5-Dimethyl-3-Piperidylfuran

4-Hydroxy-2,5-dimethyl-3-piperidylfuran is a coproduct of synthesis of 4-hydroxy-2,5-dimethyl-3(2H)furanone

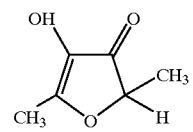

from L-rhamnose.

L-Rhamnose (1.65 mol) in anhydrous ethyl alcohol is stirred in the presence of piperidine (1 mol) and acetic acid (2.2 mol). The reaction medium is heated under reflux. The solvent and the acetic acid are removed by evaporation. The remaining reaction medium is hydrated and then basified to pH 12.5 with sodium hydroxide. The product of the reaction is extracted from the aqueous phase obtained with dichloromethane.

The reaction product contained in the dichloromethane phase is purified by washing with water and then washing with a 1 M solution of HCl until a pH of 4.5 is obtained in the aqueous phase. The dichloromethane is evaporated off in order to obtain a product having a purity greater than 95% by gas chromatography.

The product obtained is analysed as being 4-hydroxy-2,5-dimethyl-3-piperidylfuran having a molecular weight of 195 g/mol.

EXAMPLE 2

Flavour Enhancing Property

The 4-hydroxy-2,5-dimethyl-3-piperidylfuran obtained according to Example 1 is combined with 4-hydroxy-2,5-dimethyl-3(2H)furanone (strawberry, caramel, pineapple flavour), at a concentration of 8 to 20 ppm in the edible finished product, the (4-hydroxy-2,5-dimethyl-3-piperidylfuran)/(4-hydroxy-2,5-dimethyl-3(2H)furanone) ratio being about 3 to 4%.

The 4-hydroxy-2,5-dimethyl-3-piperidylfuran makes it possible to intensify the flavour of 4-hydroxy-2,5-dimethyl-3(2H)furanone.

What is claimed is:

1. A compound of formula I:

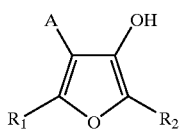

(I)

wherein A is a piperidin-1-yl group which is unsubstituted or substituted with one or more groups chosen from a ($C_1$–$C_4$) alkyl group and a hydroxyl group;

$R_1$ and $R_2$, which are identical or different, are chosen from a hydrogen atom, a ($C_1$–$C_4$)alkyl group and a hydroxyl group;

or an edible salt thereof.

2. The compound according to claim 1, which is 4-hydroxy-2,5-dimethyl-3-piperidylfuran.

3. Process for the preparation of a compound of formula I according to claim 1, which consists in reacting a piperidine of formula AH, where A is as defined in claim 1, with a compound of formula II:

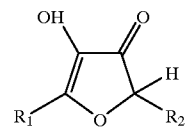

(II)

wherein $R_1$ and $R_2$, which are identical or different, are chosen from a hydrogen atom, a ($C_1$-$C_4$)alkyl group and a hydroxyl group, in order to obtain a compound of formula I as defined above.

4. Process according to claim 3, characterized in that the said compound of formula II is 4-hydroxy-2,5-dimethyl-3(2H)furanone and the said compound of formula I is 4-hydroxy-2,5-dimethyl-3-piperidylfuran.

5. Process according to claim 3, wherein L-rhamnose is reacted with piperidine to give 4-hydroxy-2,5-dimethyl-3(2H)furanone and 4-hydroxy-2,5-dimethyl-3-piperidylfuran.

6. The method of enhancing flavour comprises administering a flavour enhancing effective amount of a compound or an edible salt thereof, according to claim 1.

7. The method of claim 6, wherein the compound is combined with at least one flavour.

8. The method according to claim 7, wherein the compound is 4-hydroxy-2,5-dimethyl-3(2H)furanone.

9. A composition comprising a flavour enhancing effective amount of a compound according to claim 1, in combination with at least one flavour, in a solvent.

10. The composition according to claim 9, wherein the compound is present in a proportion of 1 to 10% relative to the flavour.

* * * * *